United States Patent [19]

Kruse et al.

[11] 4,313,000
[45] Jan. 26, 1982

[54] PROCESS FOR PREPARING 5-(2-CHLORO-4-TRIFLUOROMETHYL-PHENOXY)-2-NITRO-N-ALKANESULPHONYL BENZAMIDES FROM A TOLUENE DERIVATIVE AND INTERMEDIATES

[75] Inventors: Walter M. Kruse, Wilmington, Del.; John F. Stephen, West Chester, Pa.

[73] Assignee: ICI Americas Inc., Wilmington, Del.

[21] Appl. No.: 250,204

[22] Filed: Apr. 2, 1981

[51] Int. Cl.³ .................. C07C 103/76; C07C 102/00
[52] U.S. Cl. ...................................... 564/99; 260/401; 71/103; 544/92; 560/27; 564/430
[58] Field of Search ........................... 564/99; 260/401

[56] References Cited

U.S. PATENT DOCUMENTS 3,840,597 10/1974 Moore et al. ............... 564/99 X
3,856,859 12/1974 Moore et al. ............... 564/99

FOREIGN PATENT DOCUMENTS 3416 8/1979 European Pat. Off. ............ 71/103

OTHER PUBLICATIONS

CA 91:175034v (1979).
CA 90:151815d (1978).

Primary Examiner—Thomas A. Waltz
Attorney, Agent, or Firm—John M. Sheehan; David J. Levy

[57] ABSTRACT

The invention comprises the preparation of a compound of the following formula (I):

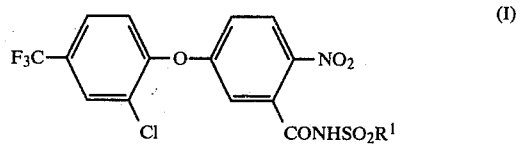

wherein $R^1$ is alkyl of 1 to 12 carbons, from the compound of the following formula (II):

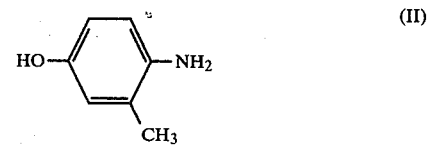

by the steps of coupling (II) with 3,4-dichlorobenzotrifluoride; reacting the —NH₂ group with an XCOOR compound, X being a leaving group with R an organic moiety; oxidizing the —CH₃ group to a —COOH group; cyclization to produce a heterocycle with loss —OR; opening the heterocycle with an alkanesulphonamide; and oxidizing the resultant —NH₂ group to an NO₂ to yield a compound of formula (I). Novel intermediates are also described. Compounds of formula (I) are useful as selective pre- and post-emergent herbicides.

9 Claims, No Drawings

PROCESS FOR PREPARING 5-(2-CHLORO-4-TRIFLUOROMETHYLPHENOXY)-2-NITRO-N-ALKANESULPHONYL BENZAMIDES FROM A TOLUENE DERIVATIVE AND INTERMEDIATES

SUMMARY OF THE INVENTION

The invention comprises the preparation of a compound of the following formula (I):

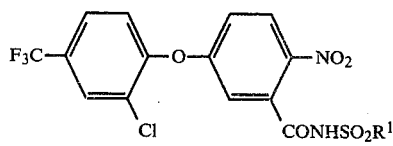

(I)

wherein $R^1$ is alkyl of 1 to 12 carbons, from the compound of the following formula (II):

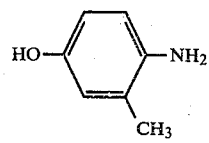

(II)

by the steps of coupling (II) with 3,4-dichlorobenzotrifluoride; reacting the —$NH_2$ group with an XCOOR compound, X being a leaving group and R an organic moiety, oxidizing the —$CH_3$ group to a —COOH group; cyclization to produce a heterocycle with loss of —OR; opening the heterocycle with an alkanesulphonamide; and oxidizing the resultant —$NH_2$ group to an $NO_2$ to yield a compound of formula (I). Additionally, novel intermediates used in the process are described.

BACKGROUND OF THE INVENTION

Compounds of the following formula (I) are useful as selective herbicides to kill undesirable plant growth among crops such as cotton, soy beans, peas, corn, wheat and rice:

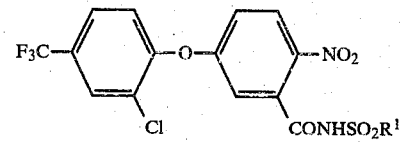

(I)

wherein $R^1$ is an alkyl group of 1 to 12 carbons, as disclosed in European patent application number 79300098.5 published Aug. 8, 1979 as publication number 3416. The compounds of formula (I) are useful both as pre- and post-emergence herbicides when applied at a rate of 0.1 to 5.0 kilograms per hectare.

Processes for the synthesis of compounds of formula (I) are known as seen by a reading of European patent publication number 3416. However, many of such processes are disadvantageous from a commercial standpoint in view of the need for nitrating a compound of a formula such as

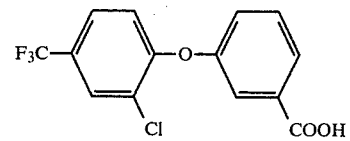

It is an object of the present invention to provide a process for the preparation of compounds of the formula (I) using 4-amino-3-methylphenol or, considering steps leading to 4-amino-3-methylphenol, ortho-nitrotoluene as the starting material. The process of the invention has the advantage of using an inexpensive starting material which has a nitrogen in place at the desired position for the nitro group of the compounds of formula (I). The method of the invention thus is in contrast to known or obvious methods for the synthesis of compounds of formula (I) which require nitrogen substitution on the ring as one of the final steps. This introduction in the prior art of a nitrogen atom on an aromatic ring may be disadvantageous in view of nitrogen atom additions at other than the described position para to the phenoxy substituent.

DETAILED DESCRIPTION OF THE INVENTION

The following is a scheme of the synthetic pathway described herein for the process of the present invention:

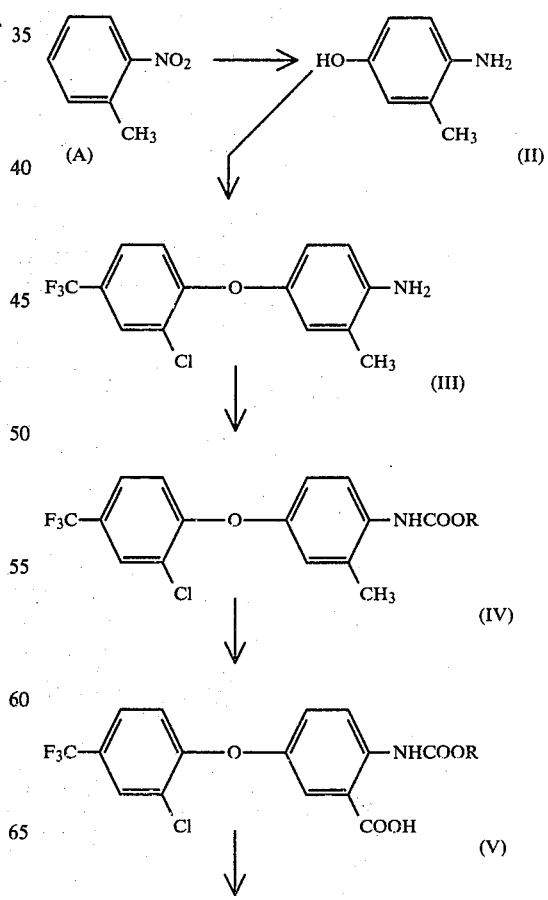

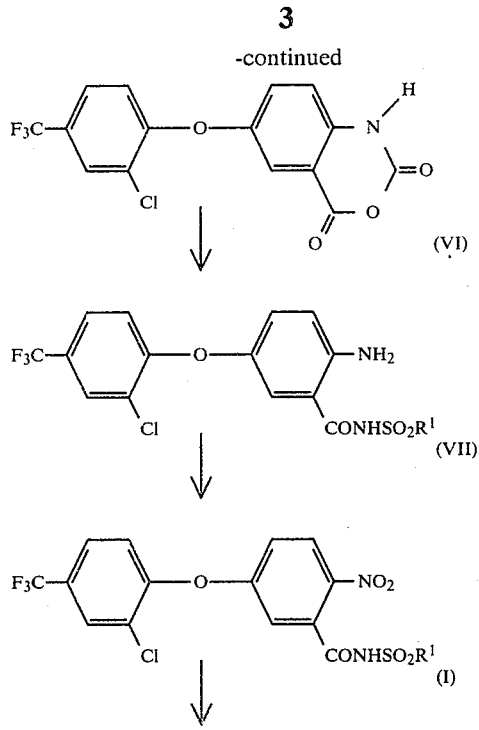

wherein R is an organic moiety and $R^1$ is alkyl of about 1 to 12 carbons.

Compound (II) is 4-amino-3-methylphenol, also known as 4-amino-meta-cresol, and is described in Beilsteins Handbuch, XIII, Vierte Auflage, page 593 (1930).

The reaction of compound (II) to produce compound (III) involves coupling of compound (II) which has two nucleophilic moieties, i.e. the HO— and —$NH_2$ groups, with 3,4-dichlorobenzotrifluoride. A significant aspect of the present invention is the coupling reaction from compound (II) to yield (III) since it has been found that coupling via the phenolic HO— group, rather than the anilinic —$NH_2$ group, is the predominant route. Coupling of compound (II) with 3,4-dichlorobenzotrifluoride is preferably done at atmospheric pressure; at about 100° to 200° C., preferably about 130° to 175° C.; at a pH of about 7 to 10, preferably about 9 as adjusted by an alkali or alkaline carbonate which can be accomplished by using a 30% to 100% molar excess of carbonate based on compound (II); in a dipolar aprotic solvent such as dimethyl sulfoxide, N-methylpyrrolidinone, N,N-dimethylformamide, N,N-dimethylacetamide or sulfolane; a molar ratio of compound (II): 3,4-dichlorobenzotrifluoride of about 1:1 to 2:1, preferably about 1.1:1; and for a period of about 15 to 24 hours.

The reaction of compound (III) with a compound of the formula XCOOR to produce (IV) is a protection step for the —$NH_2$ group in the subsequent oxidation of the —$CH_3$ group, X being a leaving group and R being an organic moiety. In more detail, X may be a halogen atom such as bromo or chloro, or lower alkoxy of about 1 to 6 carbons and R may be a lower alkyl group e.g. of about 1 to 6 carbons such as ethyl or methyl, or aryl such as phenyl. The protection of compound (III) with XCOOR is preferably done with methyl chloroformate. The reaction may be conducted at atmospheric pressure; at a temperature of about 25° to 65° C., preferably about 50° C.; in an organic solvent such as a cyclic ether or a chlorinated hyrocarbon such as tetrahydrofuran or methylene dichloride; using a slight molar excess of the compound of formula XCOOR, for example a molar ratio of XCOOR:compound of formula (III) of over 1:1 to about 1.2:1; and with a large molar excess of a weak base such as an alkali carbonate if X is a halogen so as to neutralize HX as it is formed in the reaction.

The oxidation of the methyl group of urethane compound (IV) to produce the —COOH group in compound (V) involves use of an oxidation agent or agents such as oxygen and a catalyst such as cobalt and manganese acetate or the use of a permanganate such as potassium permanganate. The permanganate reaction can be conducted at atmospheric pressure; at a temperature of about 70° to 90° C., preferably about 80° C.; at about neutral pH, a buffer such as magnesium sulfate being used if necessary; in a solvent which is not easily oxidized such as an aqueous tert-butanol solution; and with an excess of the oxidation agent. Other oxidation agent or agent and catalyst systems may be used under conditions known in the art for the oxidation system, e.g. with oxygen and cobalt acetate, a temperature of about 110° C. would be used with an acetic acid solvent.

Cyclization of a compound of formula (V) can be accomplished in a manner similar to that used for the cyclization of N-ethoxycarbonyl anthranilic acid to give isatoic anhydride as described by G. M. Coppola in Synthesis, page 505 (1980) at page 506. For example, the compound of formula (V) may be cyclized by treatment with a halogenating agent such as thionyl chloride, phosphorous tribromide or acetyl chloride. Alternatively, the cyclization may be done by heating neat or in an organic solvent such as benzene or toluene at reflux for several hours.

The use of the heterocycle (VI) conveys several advantages to the synthesis scheme. The heterocycle (VI) is a stable, easily handled material. Further, it had been projected that a separate step would be necessary to convert the —NHCOOR group back to an —$NH_2$ after the —COOH group of (V) had been converted into a —$CONHSO_2R^1$ group. Instead, deprotection occured simultaneously with formation of a sulphonamide group in the reaction of compound (VI) to yield (VII).

The reaction of compound (VI) to produce the compound of formula (VII) involves a ring opening and will take place under basic conditions with an excess of an alkanesulphonamide of the formula $H_2NSO_2R^1$, wherein $R^1$ is alkyl of about 1 to 12 carbons, preferably 1 to 4 carbons, such as methanesulphonamide. The reaction may be carried out at atmospheric pressure; at about 80° to 150° C., preferably about 100° to 120° C.; in a dipolar aprotic solvent such as N-methylpyrrolidinone, N,N-dimethylformamide, N,N-dimethylacetamide or sulfolane; at a molar ratio of the alkanesulphonamide:compound (VI) of about 1:1 to 5:1, preferably about 2:1, and with the addition of at least 1 mole, per mole of compound (VI), of an alkali metal hydroxide to provide the reactive anion of the alkanesulphonamide.

The last step of the process of the invention involves the oxidation of compound (VII) with an oxidation agent to yield a 5-(2-chloro-4-trifluoromethylphenoxy)-2-nitro-N-alkanesulphonyl benzamide of formula (I). The oxidation agent may be a peracid such as peracetic acid, perphthalic acid, permaleic acid or hydrogen peroxide may be used. Reaction conditions will depend on the particular agent but in general, the oxidation may be carried out at atmospheric pressure; at a temperature from about 25° to 90° C., preferably about 75° C.; in the presence of a mineral acid catalyst such as sulfuric or nitric acid; in a solvent such as acetic acid or a mixture of acetic acid and a chlorinated solvent such as methylene dichloride, ethylene dichloride or chlorobenzene; in a molar ratio of oxidation agent:compound of formula (VII) of about 2:1 to 8:1, preferably about 5:1; and for a period of about 5 to 20 hours.

Although the starting material of formula (II) for the process of the invention is a known compound, a further feature of the present invention is the total process for the preparation of a compound of formula (I) by starting with ortho-nitrotoluene of the formula (A):

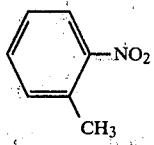
(A)

and proceeding through formula (II). This particular aspect of the invention is significant because of the use of an inexpensive and readily available starting material.

From ortho-nitrotoluene of formula (A), the synthesis may proceed by use of a Bamberger-type catalytic hydrogenation reaction by the action of hydrogen in an acidic medium using a noble group metal such as platinum, palladium, rhodium or ruthenium to produce compound (II). This particular reaction is described in detail in Japanese Kokai 76,110,528 issued to Seiko Chemical Co., Ltd on Sept. 30, 1976 and summarized in Chemical Abstracts 86 (1977) 55156m, United Kingdom Patent 713,622 published Aug. 11, 1954 in Example 9 and U.S. Pat. No. 4,051,187 issued Sept. 27, 1977.

Also within the scope of the present invention are novel intermediates used in the process of the present invention. These novel intermediate compounds are those of the formulae (III), (IV), (V), (VI) and (VII).

In the following Examples, the following abbreviations are used: g (grams); ml (milliliters); N (normal); mm (millimeters); C (centigrade); and m.p. (melting point).

EXAMPLE I

Coupling reaction to yield (III)

A slurry of 25.0 g of 4-amino-3-methylcresol of formula (II), 48.0 g of 3,4-dichlorobenzotrifluoride, 300 ml of N,N-dimethylacetamide and 20.0 g of finely ground potassium carbonate ($K_2CO_3$) is stirred and heated under nitrogen at about 130° to 140° C. for 24 hours. The product is filtered and the filter cake is washed with three 10 ml portions of methyl ethyl ketone. The filtrate is then gradually vacuum evaporated down to 1 to 4 mm Hg at 50° to 70° C.

The residue is then dissolved in 200 ml of toluene and filtered to remove a small amount of starting material. The filtrate is washed with water and vacuum evaporated to 59.6 g of product which solidifies on standing to a mixture of isomers, m.p. 48°–50°. Compounds (III) may be isolated by column chromatography using silica gel and an organic solvent such as toluene or tetrahydrofuran.

EXAMPLE II

Preparation of compound (IV), R=methyl

A solution of 10 g of compound (III) prepared as in Example I and 100 ml of methylene dichloride is prepared and 5.4 g of potassium carbonate is added thereto. To the solution is dropwise added 3.6 g of methyl chloroformate ($ClCOOCH_3$) over three minutes. During the addition, a slight exotherm and fine precipitate may be noted. The reaction mixture is then stirred for 30 minutes at room temperature, filtered and the solids are washed with methylene dichloride. The combined filtrate is then vacuum evaporated to yield 7.6 g of compound (IV) wherein R is methyl, m.p. 107°–110° C.

EXAMPLE III

Preparation of compound (V), R=methyl

A solution of 0.8 g of the compound (IV), R=methyl, from Example II and 25 ml of tert-butanol is prepared and to it is added a solution of 0.7 g $MgSO_4.7H_2O$ in 8 ml of water. To the combined stirred solution maintained at 80° C. is slowly added 1.5 g of potassium permanganate over four hours in portions. Stirring is continued for an additional hour and the reaction mixture is then filtered with separation of manganese dioxide. The $MnO_2$ is washed with 10 ml of acetone and the combined filtrates are vacuum evaporated to dryness. The product is taken up in 15 ml of acetone and added to 50 ml of a 1 molar HCl solution with stirring. The resultant precipitate is filtered off and, after drying, is found to be 0.6 g of the compound of formula (V), wherein R is methyl, m.p. 178°–181° C.

EXAMPLE IV

Preparation of compound (VI)

To a 250 ml round bottom flask is added 5 g of 2-methoxycarbonylamino-5-(2-chloro-4-trifluoromethylphenoxy)-benzoic acid of the formula (V), R=methyl, and 100 ml of thionyl chloride is added. The reaction mixture takes a red color and is stirred at about 45° C. As the solid dissolves and over 30 minutes, the color changes to a yellow-brown. After 3 hours, 2.2 g of a white solid of the formula (VI) was collected which decomposes at 240° C.

EXAMPLE V

Preparation of compound (VII), $R^1$=methyl

The potassium salt of methanesulphonamide is prepared by firstly stirring 1.43 g of methanesulphonamide in 100 ml of toluene under nitrogen. 0.74 of potassium hydroxide pellets are then added, and the mixture is then heated to reflux with removal of water as a water-toluene azeotrope. After complete water removal, the toluene is distilled off with simultaneous addition of 100 ml of dimethyl formamide (DMF), thereby producing a suspension of the potassium salt of methanesulphonamide in DMF.

The suspension is then heated to about 100° C. and a solution of 2 g of the isatoic anhydride derivative of formula (VI) product of Example IV in about 50 ml of DMF is added with stirring over one hour. The mixture is then maintained at about 100° C. for 24 hours after which the DMF is removed by distillation. The residue is then purified by chromatography using silica gel and toluene, ethyl acetate or mixtures of isopropanol and methylene chloride as the solvent to yield 2-amino-5-(2-chloro-4-trifluoromethylphenoxy)-N-methanesulphonyl benzamide having the formula (VII) wherein $R^1$ is methyl, m.p. 185°–186° C.

EXAMPLE VI

Oxidation to yield compound (I), $R^1$=methyl

A stirred solution is prepared containing 39.5 g of 2-amino-5-(2-chloro-4-trifluoromethylphenoxy)-N-methanesulphonyl benzamide prepared as in Example V, 1380 ml of glacial acetic acid and 1.0 g of concentrated nitric acid at about 40° C. To the solution is added 138 g of a 30% by weight hydrogen peroxide in water solution and the reaction mixture is raised to and maintained at about 70° C. for 20 hours. The solution is then poured slowly into about 3 liters of ice water with precipitation of crude product. After filtration, the product is isolated as a solid, m.p. 175°–183° C., containing 68% of the compound of formula (I), $R^1$=methyl, as determined by high pressure liquid chromatography, thin layer chromatography and its mass spectrum. Recrystallization from aqueous methanol yields the product 5-(2-chloro-4-trifluoromethylphenoxy)-2-nitro-N-methanesulfphonyl benzamide, m.p. 216°–218° C.

What is claimed is:

1. A method of preparing a 5-(2-chloro-4-trifluoromethylphenoxy)-2-nitro-N-alkanesulphonyl benzamide of the following formula (I):

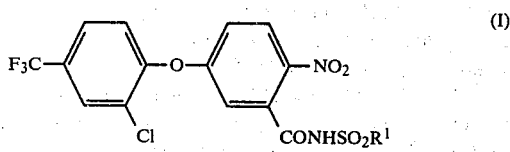

wherein $R^1$ is an alkyl group of about 1 to 12 carbons, from 4-amino-3-methylphenol of the following formula (II):

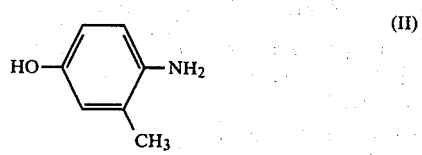

which comprises (i) reacting the phenol of formula (II) with 3,4-dichlorobenzotrifluoride to produce the aniline of the following formula (III):

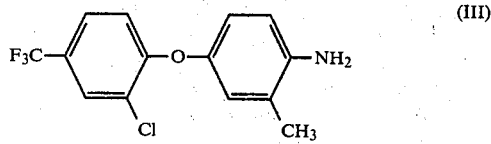

(ii) reacting the aniline of formula (III) with a compound of the formula XCOOR, wherein X is a leaving group and R is an organic moiety to produce the urethane of the following formula (IV):

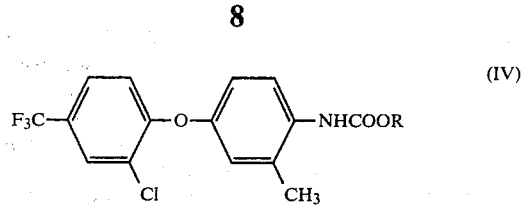

(iii) oxidizing the urethane of formula (IV) to produce the acid of the following formula (V):

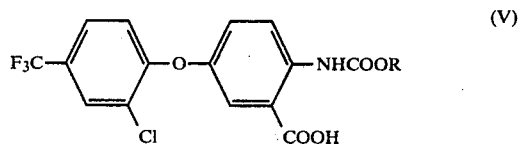

(iv) cyclizing the acid of formula (V) to produce the heterocycle of the following formula (VI):

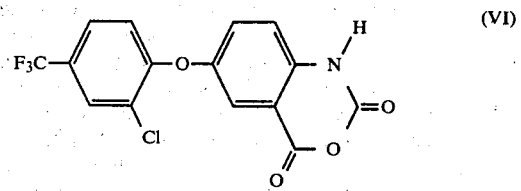

(v) reacting the heterocycle of formula (VI) with an alkanesulfphonamide of the formula $H_2NSO_2R^1$ to produce the sulphonamide of the following formula (VII):

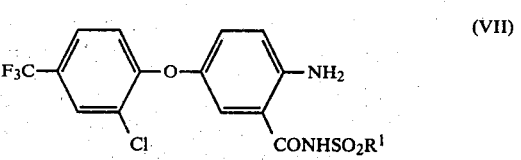

and (vi) oxidizing the sulphonamide of formula (VII) with an oxidation agent to yield the 5-(2-chloro-4-trifluoromethylphenoxy)-2-nitro-N-alkanesulphonamide of formula (I).

2. The method of claim 1, wherein the 4-amino-3-methylphenol of formula (II) is produced from ortho-nitrotoluene of the following formula (A):

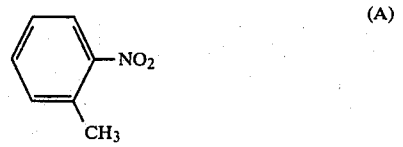

by subjecting the ortho-nitrotoluene of formula (A) to a catalytic hydrogenation in an acidic medium to produce 4-amino-3-methylphenol.

3. The method of claim 1, wherein step (i) is conducted at about 100° to 200° C.

4. The method of claim 1, wherein in step (ii), X is a halogen atom and R is a lower alkyl group.

5. The method of claim 1, wherein step (iii) is conducted using a permanganate oxidation agent.

6. The method of claim 1, wherein step (iv) is conducted using a halogenating agent.

7. The method of claim 1, wherein step (v) is conducted in the presence of an alkali metal hydroxide.

8. The method of claim 1, wherein in step (vi), said oxidation agent is hydrogen peroxide.

9. The method of claim 1, wherein $R^1$ is methyl.

* * * * *